United States Patent [19]
Jo

[11] Patent Number: 5,838,444
[45] Date of Patent: Nov. 17, 1998

[54] MAGNETO-OPTIC CHARACTERISTIC MEASURING APPARATUS

[75] Inventor: Yung Kuk Jo, Chunan-si, Rep. of Korea

[73] Assignee: SKC Limited, Kyungki-do, Rep. of Korea

[21] Appl. No.: 753,369

[22] Filed: Nov. 25, 1996

[51] Int. Cl.$^6$ .................................................. G01J 4/00
[52] U.S. Cl. .......................................... 356/369; 356/367
[58] Field of Search .................................... 356/369, 364, 356/368, 366, 362, 370

[56] References Cited

U.S. PATENT DOCUMENTS

| | | | |
|---|---|---|---|
| 4,410,277 | 10/1983 | Yamamoto et al. | 356/369 |
| 4,816,761 | 3/1989 | Josephs | 356/369 |
| 4,838,695 | 6/1989 | Mansuripur et al. | 356/369 |
| 4,922,200 | 5/1990 | Jackson et al. | 356/369 |

FOREIGN PATENT DOCUMENTS

63-122930   5/1988   Japan .

Primary Examiner—Tan Dinh
Attorney, Agent, or Firm—Richard M. Goldberg

[57] ABSTRACT

A magneto-optic characteristic measuring device which is adapted to measure a Kerr rotation angle is a kind of magneto-optic characteristic exhibited in materials used for magneto-optic recording media. Known materials exhibiting a magnetic Kerr effect have very small Kerr rotation angle ranging from about 0.1° to about 0.5°. As a result, it is difficult to accurately measure such a small Kerr rotation angle using known measuring devices due to an influence caused by noise components. In the magneto-optic characteristic measuring apparatus, its electronic circuit unit, which serves to magneto-optically modulate a laser beam from an optical unit introduced in a beam splitter via a polarizer and to record the modulated beam in an X-Y recorder using a detect signal from an optical detector unit, includes a lock-in amplifier,.thereby accurately measuring a small Kerr rotation angle.

4 Claims, 6 Drawing Sheets

FIG. 1

FIG. 2A polar kerr effect

FIG. 2B longitudinal kerr effect

FIG. 2C transverse kerr effect

FIG. 7A sample 1-1

FIG. 7B sample 1-2

FIG. 8A sample 2-1

FIG. 7C sample 1-3

FIG. 8B sample 2-2

FIG. 8C sample 2-3

MAGNETO-OPTIC CHARACTERISTIC MEASURING APPARATUS

BACKGROUND OF THE INVENTION

1. Field of the Invention

The present invention relates to a magneto-optic characteristic testing apparatus, and more particularly to a magneto-optic characteristic measuring apparatus which is adapted to measure a Kerr rotation angle which is a kind of magneto-optic characteristic exhibited in materials used for magneto-optic recording media.

2. Description of the Prior Art

Generally, magneto-optic disks are used in a magnetic recording system which irradiates a laser onto selected portions of a magnetic thin film coated over a disk substrate to increase the temperature of the selected portions, and then changes the magnetization direction of the temperature-increased selected portion, thereby recording information on those portions.

A magneto-optic effect is utilized upon reproducing information stored in such magneto-optic disks. Here, the magneto-optic effect means that the polarization direction of laser rotates in accordance with the magnetization direction. This will be described in more detail.

When a linearly polarized light beam is inclinedly incident on a substance, a beam reflecting from the substance based on the incident beam becomes typically an elliptically polarized beam which has a major-axis direction rotated from the polarization direction of the incident beam.

Such a phenomenon is utilized in deriving optical constants, such as n and k, of materials and measuring the thickness of a thin film.

However, such a phenomenon does not occur when light is vertically incident on an isotropic material.

Figure 1:
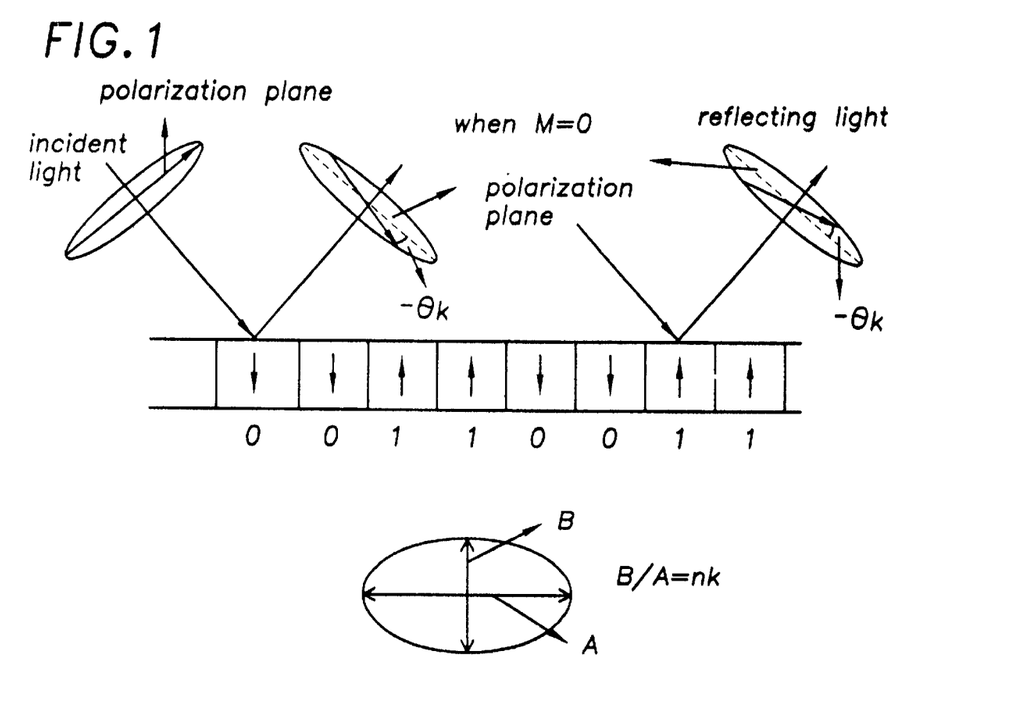
FIG. 1 is a view explaining a variation in Kerr rotation angle ($\theta_k$) depending on the direction of magnetization and a Kerr ellipticity (nk)

Meanwhile, when a linearly polarized light beam is vertically incident on a magnetized material, an elliptically polarized beam having a major-axis direction rotated from the polarization direction of the incident beam reflects from the material based on the incident beam, as shown in FIG. 1. Such a phenomenon is called "a Kerr effect". The magnetic polarization angle in this case is called "a Kerr rotation angle, $\theta_k$," whereas the ratio between the longer and shorter axes of the elliptically polarized beam is called "a Kerr ellipticity", nk.

In this case, the rotation direction is to the right when the incidence direction of the incident beam is identical to the magnetization direction whereas it is to the left when the incidence direction of the incident beam is reverse to the magnetization direction. In the latter case, $\theta_k$ and $_nk$ are prefixed with a "–(minus)" symbol.

Figure 2A:
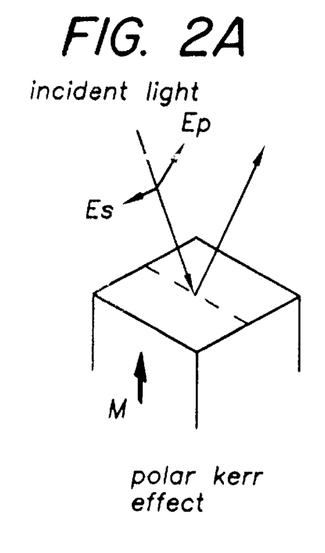
FIGS. 2A–2C are views explaining a Kerr effect.
Figure 2B:
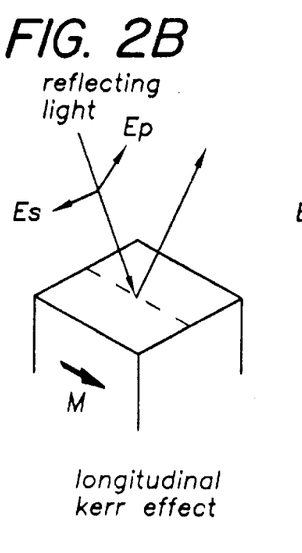
Figure 2C:
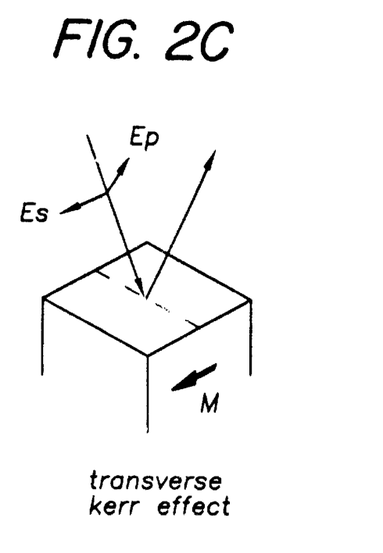

As shown in FIG. 2A–2C, there are three kinds of Kerr effects, namely, polar, longitudinal and transverse Kerr effects. For magneto-optic recording media, the polar Kerr effect is utilized which is exhibited in the case of a magnetization parallel to a direction tangential to the reflection surface.

In FIGS. 1 and 2A–2C, the reference character M denotes the direction and strength of the magnetization.

When information is recorded on a recording film exhibiting a magnetic Kerr effect, noise is generated in addition to signals reproduced. The ratio of reproduced signals to noise, namely, signal-to-noise ratio (S/N ratio) is expressed as follows:

$$S/N \propto \sqrt{R} \cdot \theta_k$$

That is, the S/N ratio is proportional to the reflection factor of the recording film and the Kerr rotation angle. Accordingly, it is very important to accurately evaluate Kerr rotation angles in the development of recording materials, the determination of optimum compositions and the determination of the film forming conditions for recording films.

Figure 3:
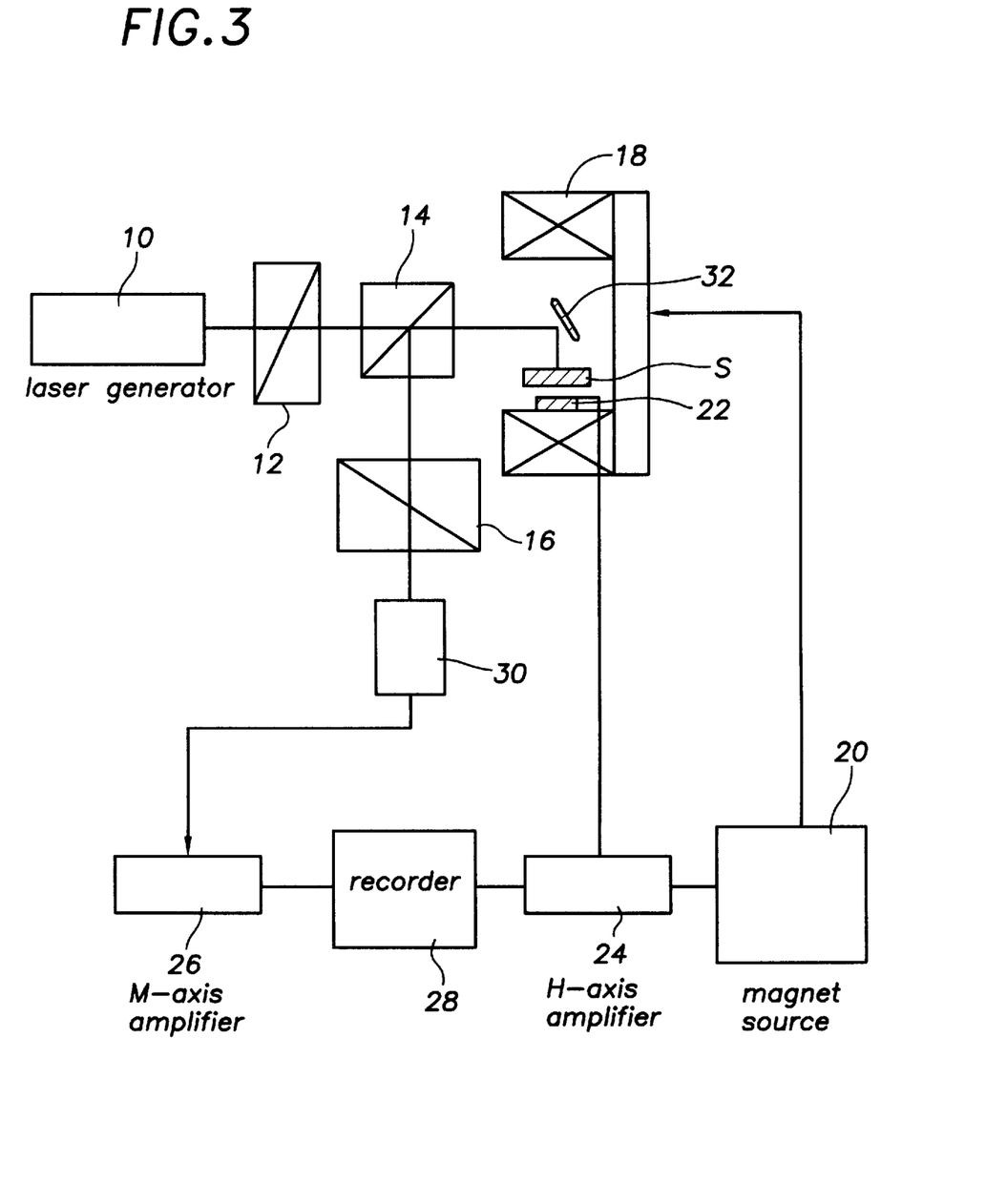
FIG. 3 is a view illustrating a conventional magneto-optic characteristic measuring device.

FIG. 3 is a view explaining a conventional magneto-optic characteristic measuring device. In FIG. 3, the reference numeral 10 denotes a laser generator.

As shown in FIG. 3, the measuring device includes a polarizer 12 which is an optical lens for polarizing a laser beam emitted from the laser generator 10 into a linearly polarized beam. That is, the polarizer 12 serves to select linearly-polarized beams from natural light, elliptically polarized beams and circularly polarized beams, thereby outputting the selected beams. Here, "linearly polarized beams" mean an electric field which vibrates in a constant direction when it is assumed that beams are electromagnetic waves.

A beam splitter 14 receives a laser beam emerging from the polarizer 12. The beam splitter 14 is an optical lens for changing the direction of a laser beam received therein. The linearly polarized beam transmits the beam to beam splitter 14 in a direction forming an angle of 90° with respect to the polarizer 12, and then to a sample S via a reflection mirror 32. Namely, the transmission direction of the linearly polarized beam is orthogonal to the polarizer 12.

The measuring device also includes an electromagnet 18 which serves to vertical magnetize a sample S. The electromagnet 18 is variable in N and S-pole directions in accordance with the flowing direction of current. A magnet source 20 is connected to he electromagnet 18. The magnet source 20 is a power source for supplying current to the electromagnet 18.

A Hall element 22 is a ranged beneath the sample S. The Hall element 22 is a magnetizing sensor adapted to generate current in a small amount in accordance with the strength and direction of the magnetization.

An H-axis amplifier 24 is coupled to the Hall element 22 to amplify a small amount of current generated from the Hall element 22 to a level at which the X-axis of an X-Y recorder 28 coupled to the H-axis amplifier 24 can float.

The measuring device also includes an optical detector 16 for receiving the beam emerging from reflection mirror 32 and the beam splitter 14 at the Kerr rotation angle, and an optical detector unit 30 for receiving the beam from the optical detector 16 and generating current, and an M-axis amplifier 26 for receiving the current from the optical detector unit 30 and amplifying it to a desired level. Since the optical detector unit 30 generates current in a small amount based on a small density of light received therein, the M-axis amplifier 26 amplifies the current to a level at which the Y-axis of the X-Y recorder 28 can float.

In FIG. 3, the reference numeral 32 denotes a reflection mirror.

Figure 4:
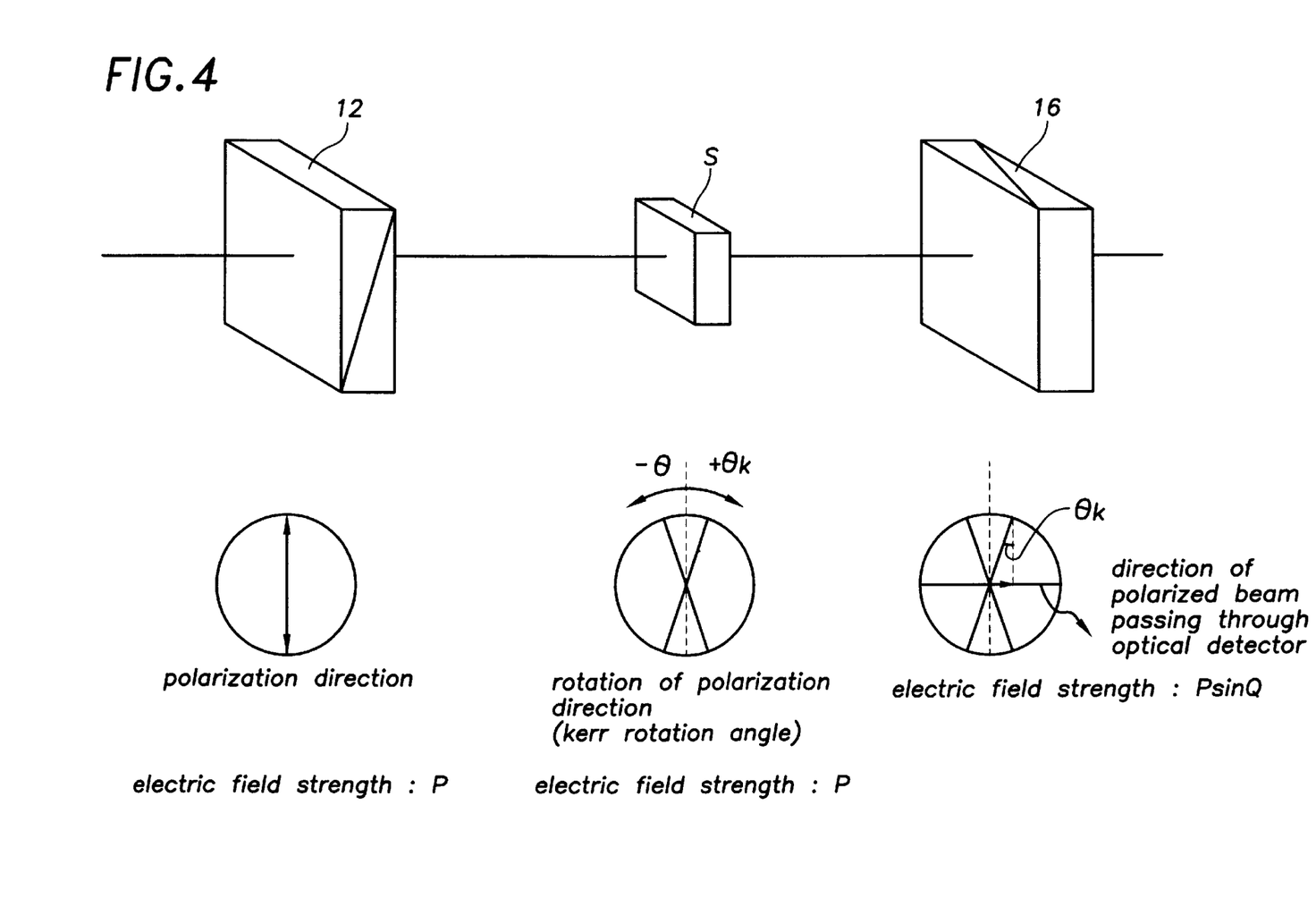
FIG. 4 is a view explaining a measuring method carried out using the conventional magneto-optic characteristic measuring device.

In the case of the conventional magneto-optic characteristic measuring device including the above-mentioned constituting elements, its operation of measuring a Kerr rotation angle resulting from a magneto-optic effect occurring when the linearly polarized beam emerging from the polarizer 12 reflects from the sample S is achieved using only a small amount of current detected by the optical detector arranged orthogonal to the polarize 12. See FIG. 4.

In this case, the optical detector unit 30 outputs a signal which is a very small amount of current. This signal can be expressed by the following equation:

$$Io = K \cdot P \cdot \sin^2 \theta + i \quad (1)$$

where, Io: Output current from the optical detector unit 30;

K: Gain of the optical detector unit 30;

P: Intensity of laser; and i: Noise based on a low extinction ratio of the polarizer.

Meanwhile, known materials exhibiting a magnetic Kerr effect have a very small Kerr rotation angle ranging from about 0.1° to about 0.5°. Accordingly, it is difficult to accurately measure such a small Kerr rotation angle using the above-mentioned conventional measuring device due to an influence caused by noise components.

SUMMARY OF THE INVENTION

The present invention has been made in view of the above-mentioned problem, and an object of the invention is to provide a magneto-optic characteristic measuring apparatus wherein its electronic circuit unit, which serves to magneto-optically modulate a laser beam from an optical unit introduced in a beam splitter via a polarizer and to record the modulated beam in an X-Y recorder using a detect signal from an optical detector unit, includes a lock-in amplifier, thereby accurately measuring a small Kerr rotation angle.

In accordance with the present invention, this object is accomplished through a magneto-optic characteristic measuring apparatus comprising a laser generator for emitting a beam of laser, a polarizer for polarizing the laser beam into a linearly polarized beam, a beam splitter for irradiating the beam from the polarizer onto a sample via a reflection mirror while receiving the reflected beam from the sample, an optical detector for receiving the reflected beam emerging from the beam splitter, an optical detector unit for receiving the beam from the optical detector, thereby generating an output signal based on the received beam, an M-axis amplifier for receiving the signal from the optical detector unit and amplifying it to a desired level, an electromagnet for applying a magnetic field to the sample, a magnet source for activating the electromagnet, a Hall element for detecting the magnetic field exerted on the sample, thereby outputting a voltage resulting from the detection, an H-axis amplifier for amplifying the voltage from the Hall element, and an X-Y recorder 28 for receiving an output signal from the M-axis amplifier at an X-axis thereof and receiving an output signal from the H-axis amplifier at an Y-axis thereof, thereby detecting a Kerr rotation angle associated with the sample, further comprising: a polarization modulator arranged between the polarizer and the beam splitter and adapted to magneto-optically modulate the laser beam emitted from the laser generator under the control of a signal generator.

BRIEF DESCRIPTION OF THE DRAWINGS

Other objects and aspects of the invention will become apparent from the following description of embodiments with reference to the accompanying drawings in which:

FIGS. 6A(*a*), 6A(*b*), 6A(*c*), 6B(*a*), 6B(*b*) and 6B(*c*) are waveform diagrams of output signals from essential elements of lock-in amplifier included in the measuring apparatus of the present invention in various states;

DETAILED DESCRIPTION OF THE PREFERRED EMBODIMENTS

Figure 5:
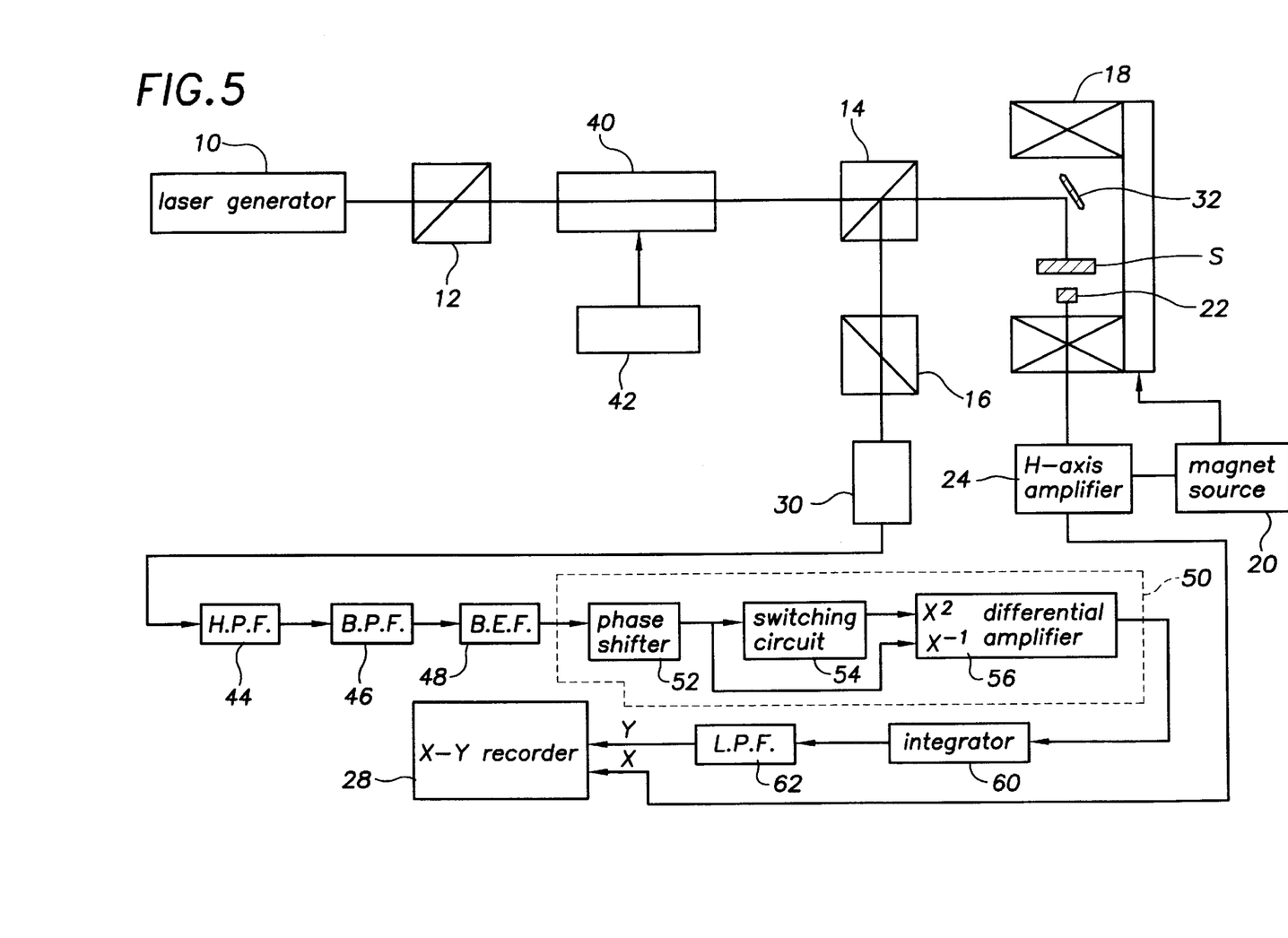
FIG. 5 is a view illustrating a magneto-optic characteristic measuring device according to the present invention.

Referring to FIG. 5, a magneto-optic characteristic measuring apparatus according to the present invention is illustrated. The magneto-optic characteristic measuring apparatus of the present invention has a configuration partially similar to that of the conventional apparatus shown in FIG. 3. For the convenience of description, elements in FIG. 5 respectively corresponding to those in FIG. 3 are denoted by the same reference numerals.

In the measuring apparatus of the present invention, a laser beam is emitted from a laser generator 10 and then sent to a beam splitter 14 via a polarizer 12. The beam emerging from the beam splitter 14 is irradiated, via reflection mirror 32, onto a sample S which, in turn, reflects the irradiated beam. The reflecting beam is sent to an optical detector 16 which sends the received beam to an optical detector unit 30. Based on the received beam, the optical detector unit 30 generates a detect signal which is, in turn,, sent to the Y-axis of an X-Y recorder 28. On the other hand, a magnetic field is applied to the sample S by an electromagnet 18 which is activated by a magnet source 20. The magnetic field is detected in the form of voltage by a Hall element 22. The voltage detected by the Hall element 22 is amplified by an H-axis amplifier 24 and then sent to the X-axis of the X-Y recorder 8. In this way, the measuring apparatus detects a Kerr rotation angle.

In accordance with the present invention, a polarization modulator 40 is arranged between the polarizer 12 and beam splitter 14. A signal generator 42 is coupled to the polarization modulator 40. The polarization modulator 40 serves to magneto-optically modulate the laser beam emitted from the laser generator 10 under control of the signal generator 42.

In accordance with the present invention, a lock-in amplifier 50 is connected to the output terminal of the optical detector unit 30 via a high-pass filter 44, a band-pass filter 46 and a notch filter or band erase filter 48 in that order. The lock-in amplifier 50 is also coupled to the Y-axis input terminal of the X-Y recorder 28 via an integrator 60 and a low-pass filter 62 in that order.

The lock-in amplifier 50 includes a phase shifter 52 for receiving an output from the notch filter 48 as its input, and a differential amplifier 56 having a first input terminal X-directly connected to the output terminal of the phase shifter 52 and a second input terminal X2 indirectly connected to the output terminal of the phase shifter 52 via a switching circuit 54. The first input terminal X-1 of the differential amplifier 56 is a "−1"-multiplication input terminal.

The polarization modulator 40 is a magneto-optic modulation unit which utilizes a Paraday rotation phenomenon.

This Paraday rotation phenomenon is a phenomenon that the polarization plane of a beam of linearly polarized light rotates by a magnetic field applied when it passes through a substance on which the magetic field is exerted. In the Paraday rotation, the rotation angle is expressed by "θ=VHL (V: Verdet constant; H: the strength of the magnetic field; and L: the length of the light path in the substance).

In this case, an electromagnet comprised of solenoid coils is used to generate the magnetic field. The direction of the magnetic field can be hanged by reversely changing the direction of current flowing through the coils. In other words, the direction of the magnetic field can be changed as the signal generator 42 sends alternating current having a frequency α to the polarization modulator 40. When no magnetic field exists, the polarization plane can vibrate left and right ("+" and "−" directions) with reference to a position where it is positioned in a state of H=0.

Where the optical detector 16 is shifted by an angle θ from the position orthogonal to the polarizer 12, the optical detector unit 30 generates an output signal expressed by the above-mentioned equation (1).

If θ is small, then the equation (1) may be expressed as follows:

$$Io = K \cdot P \cdot \theta^2 + i \quad (2)$$

Where a laser beam passing through the polarizer 12 orthogonal to the optical detector 16 reflects from a substance bearing a magneto-optic effect while being modulated at an angular velocity ω by the polarization modulator 40 arranged between the polarizer 12 and optical detector 16, θ can be expressed by the following equation (3):

$$\theta = \theta_k + \theta_m \cdot \cos(\omega t) \quad (3)$$

where, $\theta_k$: the Kerr rotation angle of the substance; and
$\theta_m$: the amplitude of the angular modulation.

In this case, the output current from the optical detector unit 30 can be expressed based on the equation (2) as follows:

$$Io = K \cdot P \cdot (\theta_k + \theta_m \cdot \cos \omega t)^2 + i \quad (4)$$

The output current can be divided by a modulation interval ω into the following components:

$$Io = I_{DC} + I_\omega + I_{2\omega} \quad (5)$$

$$I_{DC} = K \cdot P (\theta_{k2} + \theta_m^2/2) \quad (6)$$

$$I_\omega = 2K \cdot P \cdot \theta_k \cdot \theta_m \quad (7)$$

$$I_{2\omega} = K \cdot P \cdot \theta_m^2/2 \quad (8)$$

That is, the output current is divided into DC, ω and 2ω components.

The value of $\omega_k^2$ is negligible because it is very small on the order of $10^{-5}$ to $10^{-6}$.

Accordingly, the $\theta_k$ component indicative of the Kerr rotation angle based on the magneto-optic effect exists in the ω component of the output current. For this reason, a filter circuit including a variety of filters is used to leave the ω component of the output current while removing DC and 2ωcomponents. In accordance with the present invention, the filter circuit may comprise the high-pass filter 44, band-pass filter 46 and notch filter 48.

In conventional devices for measuring a magneto-optic effect, there is a noise source such as short noise of the optical detector unit 30, noise caused by a variation in laser output, and noise caused by defects of magnetic filters. Such a noise source can be removed using the above-mentioned polarization modulation method.

Now, a method for separating a θ component from the output signal from the optical detector unit 30 by use of the filter circuit will be described.

First, the output current emerging from the optical detector unit 30 passes through the high-pass filter 44 which, in turn, removes a DC component from the received current. The resultant current from the high-pass filter 44 is then sent to the band-pass filter 46, Through the band-pass filter 46, only ω components of the current are allowed to pass. In order to completely remove a 2ω component, the resultant current then passes through the notch filter 48.

In this state, it is possible to measure a very small Kerr rotation angle $\theta_k$ using the lock-in amplifier 50 which receives the current including only the θ component.

The output current emerging from the notch filter 48 has only a ω component. This current is sent to the lock-in amplifier 50. In the lock-in amplifier 50, the current passes first through the phase shifter 52 so that it can synchronize with a square wave of a frequency ω received in the switching circuit 54.

The switching circuit 54 outputs the input signal only when the square wave of the frequency ω is at a "+" level.

The signal passing through the switching circuit 54 is applied to the X2-input terminal of the differential amplifier 56, so that it is amplified to a double level. On the other hand, the signal from the phase shifter 52 not passing through the switching circuit 54 is applied to the X-1-input terminal of the differential amplifier 56, so that it is multiplied by "−1".

Figure 6A:
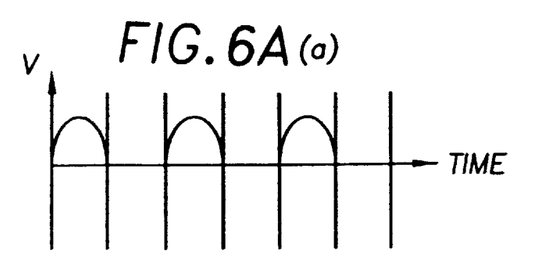
Figure 6B:
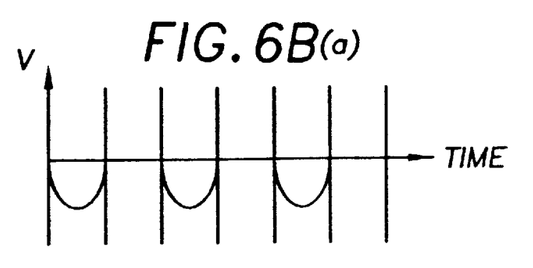

FIGS. 6A(a), 6A(b), 6A(c), 6B(a), 6B(b), and 6B(c) show waveform diagrams of output signals from the elements of the lock-in amplifier 50 in various states.

FIGS. 6A(a), 6A(b) and 6A(c) correspond to the case wherein the Kerr rotation angle $\theta_k$ has a "+" value. The waveform of FIG. 6A(a) shows the output from the switching circuit 54, the waveform of FIG. 6A(b) shows the output from the phase shifter 52, and the waveform of FIG. 6A(c) shows the output from the differential amplifier 56. On the other hand, FIGS. 6B(a), 6B(b) and 6B(c) correspond to the case wherein the Kerr rotation angle $\theta_k$ has a "−" value. The waveform of FIG. 6B(a) shows the output from the switching circuit 54, the waveform of FIG. 6B(b) shows the output from the phase shifter 52, and the waveform of FIG. 6B(c) shows the output from the differential amplifier 56.

The differentially amplified signal is then smoothed by the integrator 60. The smoothed signal has a mean value proportional to the Kerr rotation angle. Accordingly, the smoothed signal has a higher value at a larger Kerr rotation angle.

The signal smoothed by the integrator 60 is further smoothed by the low-pass filter 62 so that it can be used in the X-Y recorder 28 which is an output unit connected to the low-pass filter 62. That is, the low-pass filter 62 outputs a DC value depending on the direction and degree of the Kerr rotation angle $\theta_k$.

In this way, it is possible to amplify a ω component signal generated at a very small Kerr rotation angle ranging from 0.1° to 0.5° by use of the lock-in amplifier 50 consisting of the phase shifter 52, switching circuit 54 and differential amplifier 56. Accordingly, such a very small Kerr rotation angle can be precisely measured.

Figure 7A:
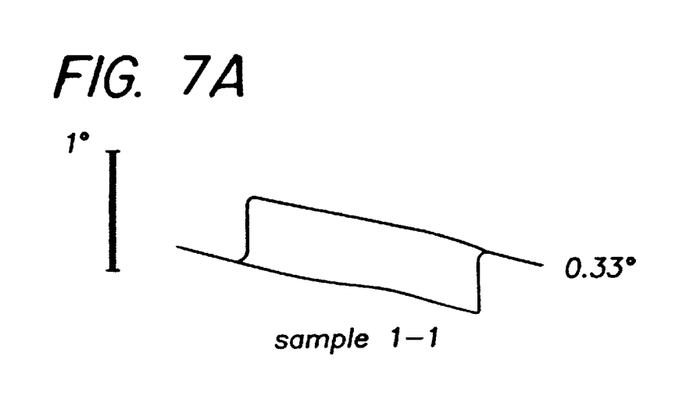
FIGS. 7A–7C are views illustrating the results of measurement in an example carried out in accordance with the present invention.
Figure 7B:
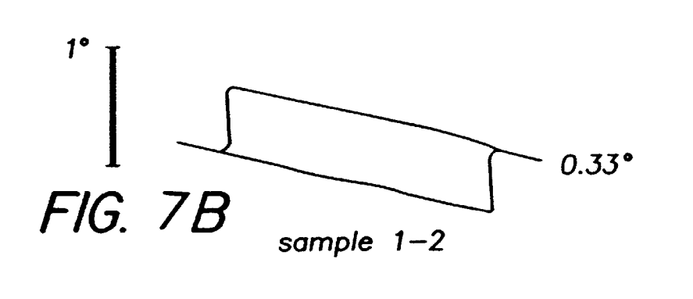
Figure 7C:
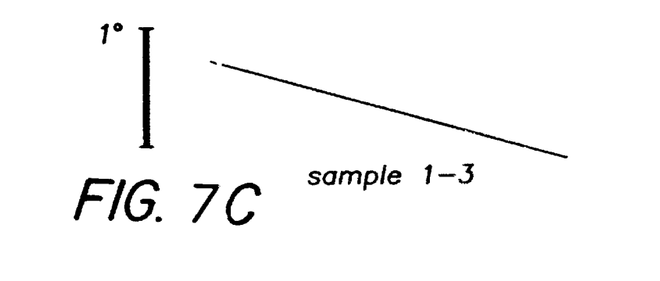

In order to evaluate the magneto-optic characteristic measuring apparatus according to the present invention, Kerr rotation angles of TbFeCo thin films having different compositions have been measured using the apparatus while varying the strength of the applied magnetic field. The results are shown in FIGS. 7A–7C.

Samples to be measured have been prepared as follows:

EXAMPLE 1

A silicon nitride (SiN) film having a thickness of 1,100 Å, a recording film having a thickness of 230 Å, another SiN film having a thickness of 400 Å and an Al film having a thickness of 300 Å were coated in a continuous manner over a polycarbonate substrate in accordance with a sputtering method. In the sputtering process, an initial vacuum of $1 \times 10^{-6}$ Torr and an Ar pressure of 2 mTorr were used.

In order to obtain a variety of samples, the composition of the recording film based on TbFeCo varied as follows:

| | Unit: Atomic Percent | | | |
|---|---|---|---|---|
| | Tb | Fe | Co | CR |
| Sample 1-1 | 21.31 | 65.30 | 10.55 | 2.84 |
| Sample 1-2 | 21.66 | 64.79 | 10.63 | 2.91 |
| Sample 1-3 | 22.13 | 65.24 | 10.67 | 2.96 |

For the prepared samples, the measurement of Kerr rotation angles of TbFeCo thin films having different compositions was conducted using the magneto-optic characteristic measuring apparatus of the present invention while varying the strength of the applied magnetic field. The results are shown in FIGS. 7A–7C, mentioned above.

In this case, the samples 1-1 and 1-2 were evaluated to have a Kerr rotation angle of 0.33°. On the other hand, no Kerr rotation angle was measured in the case of the sample 1-3 because this sample has a complimented composition exhibiting an infinite coercive force, Hc. It is impossible to magnetize the recording material exhibiting such an infinite coercive force using only a magnetic field of about 10 Koe.

EXAMPLE 2

Samples were prepared in the same manner as that used in Example 1 while varying their recording films in the basic TbFeCo composition. In this example, however, some of the recording films were adjusted in composition so as to contain Zr of 9.73 atomic percent or Pt of 12.1 atomic percent. In the case of the sample 2-1, its recording film was subjected to an oxidation during the sputtering process.

| | Unit: Atomic Percent | | | | |
|---|---|---|---|---|---|
| | Tb | Fe | Co | ZR | Pt |
| Sample 2-1 | 24.08 | 68.23 | 7.69 | | |
| Sample 2-2 | 22.52 | 60.78 | 7.15 | 9.73 | |
| Sample 2-3 | 21.47 | 60.04 | 6.39 | | 12.1 |

Figure 8A:
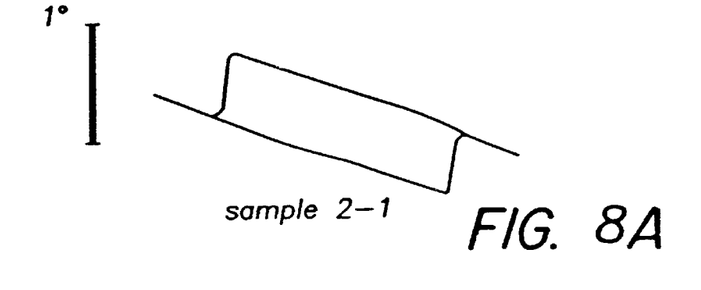
FIGS. 8A–8C are views illustrating the results of measurement in another example carried out in accordance with the present invention.
Figure 8B:
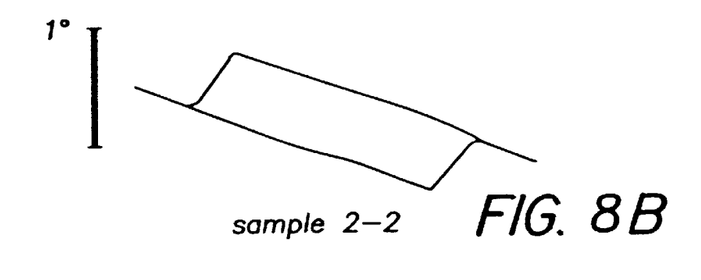
Figure 8C:
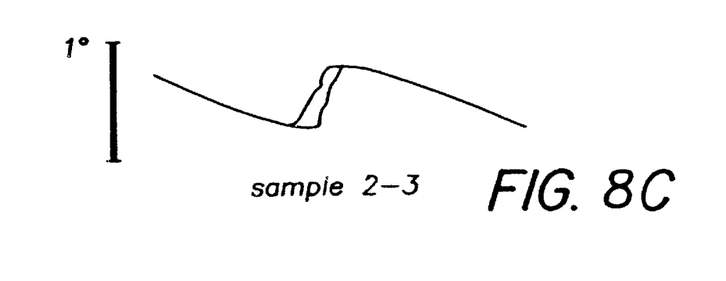

For the prepared samples, the measurement of Kerr rotation angles of TbFeCo thin films having different compositions was conducted using the magneto-optic characteristic measuring apparatus of the present invention while varying the strength of the applied magnetic field. The results are shown in FIGS. 8A–8C.

In this case, the samples 2-1 and 2-2 exhibited Kerr rotation angles of 0.33°. and 0.28°, respectively. On the other hand, no magneto-optic effect was obtained in the sample 2-3 because this sample was alloyed with a large amount of Pt.

Although the preferred embodiments of the invention have been disclosed for illustrative purposes, those skilled in the art will appreciate that various modifications, additions and substitutions are possible, without departing from the scope and spirit of the invention as disclosed in the accompanying claims.

What is claimed is:

1. A magneto-optic characteristic measuring apparatus comprising:

a laser generator for emitting a beam of laser, a polarizer for polarizing the laser beam into a linearly polarized beam, a beam splitter for irradiating the beam from the polarizer onto a sample via a reflection mirror while receiving the reflected beam from the sample, an optical detector for receiving the reflected beam emerging from the beam splitter, an optical detector unit for receiving the beam from the optical detector, thereby generating an output signal based on the received beam, an electromagnet for applying a magnetic field to the sample, a magnet source for activating the electromagnet, a Hall element for detecting the magnetic field exerted on the sample, thereby outputting a voltage resulting from the detection, an H-axis amplifier for amplifying the voltage from the Hall element, an X-Y recorder for receiving an output signal from the H-axis amplifier at an X-axis thereof and receiving an output signal from the optical detector unit at a Y-axis thereof, thereby detecting a Kerr rotation angle associated with the sample, a polarization modulator arranged between the polarizer and the beam splitter and adapted to magneto-optically modulate the laser beam emitted from the laser generator under the control of a signal generator.

2. The magneto-optic characteristic measuring apparatus in accordance with claim 1, further comprising:

a lock-in amplifier connected to the output terminal of the optical detector unit via a high-pass filter, a band-pass filter and a notch filter in that order, the lock-in amplifier being also coupled to the Y-axis input terminal of the X-Y recorder via an integrator and a low-pass filter in that order.

3. The magneto-optic characteristic measuring apparatus in accordance with claim 2, wherein the lock-in amplifier comprises:

a phase shifter for receiving an output from the notch filter as its input;

a differential amplifier having a first input terminal directly connected to the output terminal of the phase shifter and a second input terminal indirectly connected to the output terminal of the phase shifter via a switching circuit, the first input terminal being a "−1"-multiplication input terminal.

4. The magneto-optic characteristic measuring apparatus accordance with claim 2, wherein the differential amplifier is adapted to amplify an input: at the second input terminal thereof received from the switching circuit to a double level while multiplying an input at the first input terminal thereof received from the phase shifter by "−1".

* * * * *

UNITED STATES PATENT AND TRADEMARK OFFICE
CERTIFICATE OF CORRECTION

PATENT NO. : 5,838,444
DATED : November 17, 1998
INVENTOR(S) : Yung Kuk Jo

It is certified that error appears in the above-indentified patent and that said Letters Patent is hereby corrected as shown below:

Title page, insert item [30] Priority data as follows:

Nov. 27, 1995........Korea..........95-43995

Signed and Sealed this

Twenty-third Day of March, 1999

Attest:

Q. TODD DICKINSON

*Attesting Officer*   *Acting Commissioner of Patents and Trademarks*